United States Patent
Goudaliez et al.

(10) Patent No.: US 7,060,183 B1
(45) Date of Patent: Jun. 13, 2006

(54) UNIT FOR FILTERING A FLUID

(75) Inventors: Francis Goudaliez, Faches-Thumesnil (FR); Thierry Verpoort, Mouvaux (FR)

(73) Assignee: MacoPharma, Mouvaux (FR)

( * ) Notice: Subject to any disclaimer, the term of this patent is extended or adjusted under 35 U.S.C. 154(b) by 81 days.

(21) Appl. No.: 10/149,665

(22) PCT Filed: Oct. 25, 2000

(86) PCT No.: PCT/FR00/02969

§ 371 (c)(1),
(2), (4) Date: Jun. 13, 2002

(87) PCT Pub. No.: WO01/41836

PCT Pub. Date: Jun. 14, 2001

(30) Foreign Application Priority Data

Dec. 10, 1999 (FR) .......................... 99 15616

(51) Int. Cl.
*B01D 35/00* (2006.01)

(52) U.S. Cl. .............. 210/232; 210/435; 210/445; 210/453; 210/455; 210/483

(58) Field of Classification Search ............ 210/232, 210/435, 445, 453, 455, 483
See application file for complete search history.

(56) References Cited

U.S. PATENT DOCUMENTS

| | | | |
|---|---|---|---|
| 4,035,304 A | * | 7/1977 | Watanabe ................ 210/317 |
| 4,701,267 A | | 10/1987 | Watanabe et al. ........... 210/806 |
| 4,710,297 A | | 12/1987 | Suzuki et al. |
| 4,925,572 A | | 5/1990 | Pall ............................ 210/767 |
| 4,985,153 A | | 1/1991 | Kuroda et al. .............. 210/782 |
| 5,234,593 A | | 8/1993 | Kuroki et al. .............. 210/496 |
| 5,344,561 A | | 9/1994 | Pall et al. |
| 5,478,470 A | | 12/1995 | Fukuda et al. ............ 210/500.1 |
| 5,665,233 A | | 9/1997 | Fukuda et al. .............. 210/483 |
| 6,197,207 B1 | | 3/2001 | Chapman et al. ........... 210/767 |

FOREIGN PATENT DOCUMENTS

| | | |
|---|---|---|
| EP | 0 526 678 A | 2/1993 |
| EP | 0 953 361 A | 11/1999 |
| WO | WO 98 19722 A | 5/1998 |

* cited by examiner

*Primary Examiner*—W. L. Walker
*Assistant Examiner*—K S Menon
(74) *Attorney, Agent, or Firm*—Baker Botts L.L.P.

(57) ABSTRACT

A filtering unit, which may be used to filter blood or blood components to remove leukocytes. The filtering unit includes a rigid outer casing connected to a filter medium by an impermeable association means to define two compartments. The association means may be flexible and may be disposed around the filter medium. The filtering unit may additionally include a pre-filter and a post-filter.

11 Claims, 1 Drawing Sheet

UNIT FOR FILTERING A FLUID

Figure 1:
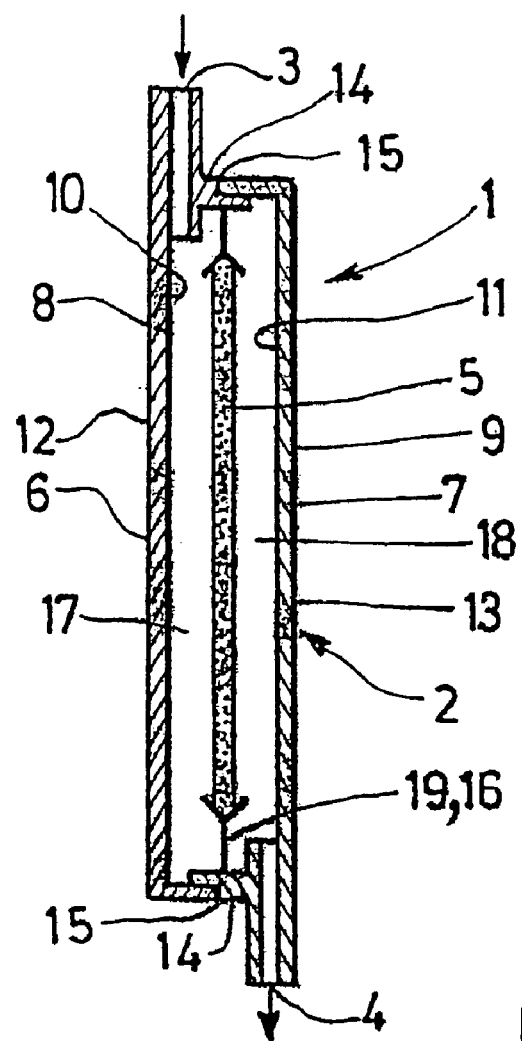

The present application claims priority under 35 U.S.C. § 365(c) to PCT/FR00/02969, filed Oct. 25, 2000 and under 35 U.S.C. § 119(d) to FR 99/15616 filed Dec. 10, 1999.

The invention relates to a filter unit serving to make it possible to filter a fluid in sterile manner.

It is typically applicable to filtering blood or components of blood under sterile conditions for the purpose of filtering out the leukocytes.

Filter units are already known that comprise a rigid housing in which the filter medium is disposed, in particular by compressing said filter medium between two portions of the housing.

But such filter units cannot be sterilized by dry or wet heat without running the risk of deforming the rigid housing, giving rise to the filter medium being locally decompressed, thereby forming preferred passageways for the fluid during filtering.

For example, when sterilization is by steam, and is therefore generally performed at 121° C., the leaktightness between the rigid housing and the filter medium might no longer be sufficient, so that some of the fluid passes through the unit without being filtered.

Document EP-A-0 526 678 describes a filter unit having a flexible bag which makes it possible to solve that problem.

But that unit, unlike a unit having a rigid housing, does not make it possible to obtain a filtered fluid flow rate to that is substantially constant because it has a volume situated upstream from the filter medium that varies.

A constant flow rate is desirable, in particular when the flow rate influences the result of the filtering.

An object of the invention is thus to remedy those drawbacks by providing a filter unit that can be sterilized by dry or wet heat without running the risk of preferred passageways appearing, and that makes it possible to deliver the filtered fluid at a substantially constant flow rate.

To this end, the invention provides a filter unit serving to make it possible to filter a fluid in sterile manner, the filter unit being of the type comprising a rigid outer casing provided with at least one inlet orifice and with at least one outlet orifice, the casing enclosing a filter medium, the filter unit further comprising separate impermeable association means which connect the outer casing to the filter medium so as to define two compartments, namely an inlet compartment and an outlet compartment, of the filter unit.

The association means, which, in particular, are deformable and flexible, are sealed firstly to the vicinity of the outer periphery of the filter medium and secondly to the inside wall of the rigid outer casing.

In another embodiment, the association means comprise a bead of adhesive disposed between the outer periphery of the filter medium and the inside wall of the rigid outer casing.

In an embodiment, the association means comprise a flexible frame in which the filter medium is held. For example, the flexible frame may be made up of two flexible sheets provided with openings and between which the filter medium is placed.

In a variant, the sheets making up the frame are fixed together around the periphery of the filter medium, e.g. by a bead of sealing formed through the filter medium.

In one embodiment, a pre-filter and/or a post-filter is/are disposed against the filter medium, respectively on the side facing into the inlet compartment and on the side facing into the outlet compartment of the filter unit.

Figure 2:
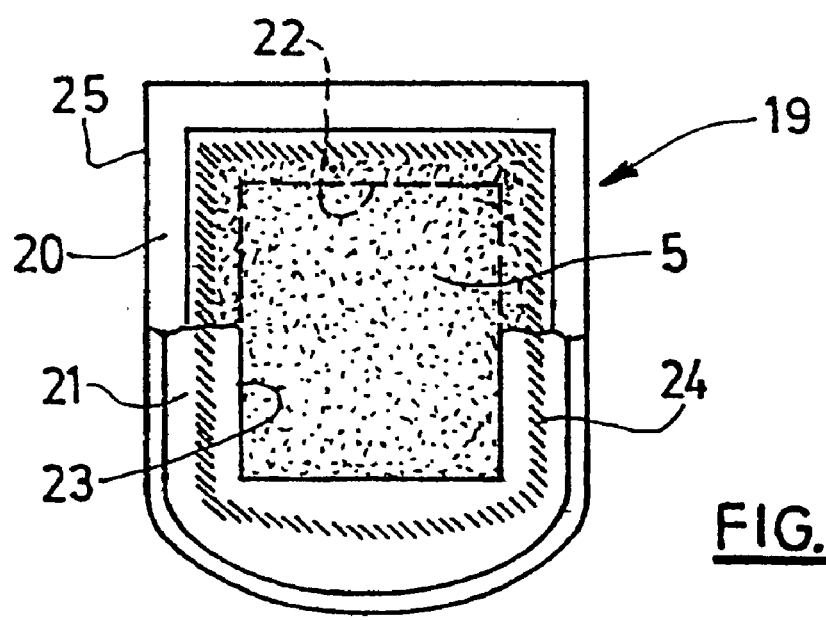

Other objects and advantages of the invention will appear on reading the following description given with reference to the accompanying drawing, in which:

FIG. 1 is a side view in longitudinal section of an embodiment of the filter unit; and FIG. 2 is a front view partially in longitudinal section of the association means of the embodiment of FIG. 1, showing in particular how the filter medium is assembled in a flexible frame.

A filter unit 1 serving to make it possible to filter a fluid typically comprises an outer casing 2 provided with at least one inlet orifice 3 and with at least one outlet orifice 4, the casing 2 enclosing a filter medium 5.

In the description, the terms "inlet" and "outlet" are defined relative to the direction in which the fluid flows through the filter unit 1 (see the arrows shown in FIG. 1) and the terms "inner" and "outer" (and "inside" and "outside") are defined relative to the assembled filter unit 1.

In a particular embodiment, the fluid is a biological fluid, in particular blood or at least one component of blood, and the filter medium 5 makes it possible to retain leukocytes.

For this purpose, a pre-filter and/or a post-filter may be disposed against the filter medium 5 so as to improve the depletion of the leukocytes in the fluid.

The filter unit 1 is designed to be incorporated, in particular via tubes connected respectively to the inlet orifice 3 and to the outlet orifice 4, in a system that, for example, comprises medical-use bags, tubes, clamps, or other filter units.

In such a system, the filter unit 1 is disposed in the path of the flow of the fluid so that the fluid enters the filter unit via the inlet orifice 3, and so that the filtered fluid is delivered via the outlet orifice 4.

In a particular example, such a system makes it possible to filter the blood as a whole, and then to centrifuge the filtered blood so as to make it possible to separate it into its various component parts. To this end, the filter unit 1 is connected via its inlet 3 to a collection bag for collecting the blood as a whole, and via its outlet 4 to a set of satellite bags. This system thus forms a closed circuit.

These various systems are not described in any more detail insofar as they include a filter unit 1 of the structure described herein.

Prior to being used, the filter unit 1 and/or the system that incorporates it may have undergone sterilization with steam so as to guarantee that the fluid is filtered in sterile manner. This step is used in particular when the system includes a collection bag containing an anticoagulant solution or a preservative solution.

With reference to FIG. 1, a description follows of an embodiment of the filter unit 1 including a rigid casing 2 formed by an assembly made up of two complementary half shells 6, 7, e.g. made of a rigid plastics material such as polycarbonate.

Each half shell 6, 7 comprises a side wall 8, 9 having an outside face 12, 13, and an inside face 10, 11 at the end of which an orifice 3, 4 is formed that extends substantially parallel to the wall 8, 9.

On each half shell 6, 7, a first fixing flange 14 and a second fixing flange 15 are formed firstly on a face of the orifice 3, 4 that is opposite from the wall 8, 9, and secondly at the end of the inside face 10, 11 of the wall 8, 9 that is opposite from the orifice 3, 4. For example, the shape of the first flange 14 is complementary to the shape of the second flange 15.

The two complementary half shells 6, 7 are disposed head-to-tail with their respective fixing flanges 14, 15 facing one other, the first flange 14 of the first half shell 6 being in contact with the second flange 15 of the second half shell 7, and vice versa.

For example, the two half shells 6, 7 are assembled together by sealing or by an adhesive, so that the volume of the filter unit 1 defined between the two inside surfaces 10, 11 of each wall 8, 9 communicates with the outside via the two orifices 3, 4 only.

The filter unit 1 includes a filter medium 5 connected to the outer casing 2 via separate impermeable association means 16 so as to define two compartments, namely an inlet compartment 17 and an outlet compartment 18, of the filter unit 1. In this configuration, the fluid communication between the two compartments 17, 18 is achieved exclusively through the filter medium 5.

The inlet compartment 17 communicates with the outside of the filter unit 1 via an inlet tube that serves to fill it with the fluid.

The outlet compartment 18 communicates with the outside of the filter unit 1 via an outlet tube that serves to deliver the filtered fluid.

The structure of the filter unit 1 thus makes it possible for the fluid to be received in the inlet compartment 17 via the inlet orifice 3, and to pass through the filter medium 5, and the filtered fluid is received in the outlet compartment 18 for delivery via the outlet orifice 4.

In one embodiment, the inlet and/or outlet tubes are flexible, breakable, and sealable.

When a set of satellite bags are associated with the outlet tube, this embodiment makes it possible, after the filter unit 1 has been dissociated by cutting and sealing off the outlet tube, to centrifuge the set of satellite bags so as to separate the various components of the blood.

With reference to FIG. 2, a description follows of an embodiment of the separate impermeable association means 16.

The term "separate means" is used in particular to indicate that the association means 16 are made of a material of a type different from the material of the filter medium 5, and that they are associated with the filter medium 5.

In the particular example, the association means 16 are flexible.

The association means 16 shown in FIG. 2 are constituted by a flexible frame 19 formed by assembling together two impermeable sheets 20, 21, e.g. made of PVC, between which the filter medium 5 is placed.

Each of these two sheets 20, 21 is provided with at least one opening 22, 23 through its central portion to enable the fluid being filtered to pass through.

The two sheets 20, 21 are fixed together, preferably around the periphery of the filter medium 5, e.g. by a bead of sealing 24 formed through the filter medium 5, and both fixing the filter medium 5 and also providing sealing between the inlet compartment 17 and the outlet compartment 18 of the filter unit 1.

The sheets 20, 21 being sealed together through the filter medium 5 generates compression, forming a leaktight bead around the filter medium 5.

The assembly formed by the filter medium 5 and by the association means 16 is connected to the outer casing 2, e.g. by using ultrasonic sealing or adhesive to bond the end 25 of the association means 16 that is opposite from the filter medium 5 to the wall of the outer casing 2.

In one embodiment (not shown), the two sheets 20, 21 forming the association means 16 are not identical, so that a first sheet 20, 21 is connected to the outer casing 2 while the other sheet is merely associated with said first sheet.

When the association means 16 are bonded by adhesive to the outer casing 2, it is possible to provide a bead of adhesive, e.g. of the silicone type, over the periphery of the association means 16 so as to improve the leaktightness of the bonding.

In FIG. 1, the bonding is formed on the inside face of the rigid wall in the vicinities of the joins between the respective flanges 14, 15 of the half shells 6, 7.

In one embodiment (not shown) the association means 16 may be nipped in leaktight manner between the two half shells 6, 7 when they are associated with each other. Since the association means 16 are impermeable, no preferred passageway for the fluid is observed after sterilization with steam has been performed, unlike when the filter medium 5 is compressed directly between two half shells.

In another embodiment (not shown), the association means 16 are formed by a bead of adhesive, e.g. of the silicone type, disposed between the periphery of the filter medium 5 and the inside face of the rigid wall, so as both to fix the filter medium 5 and also to provide sealing between the inlet compartment 17 and the outlet compartment 18 of the filter unit 1.

A brief description follows of the method of assembling the filter unit 1 shown in FIG. 1.

The association means 16, as fixed to the filter medium 5, are associated with a first half shell 6, in particular by ultrasonic sealing or by bonding with an adhesive.

The second half shell 7 is then disposed head-to-tail on the first half shell 6, with the respective fixing flanges 14, 15 facing one another.

The two half shells 6, 7 are then mutually associated in leaktight manner by ultrasonic sealing or by means of an adhesive.

The resulting filter unit 1 thus makes it possible to offer the advantages of the rigid housing, in particular by delivering a substantially constant flow rate during filtering, while also being capable of being sterilized by dry or wet heat without inducing preferred passageways for fluid during filtering.

What is claimed is:

1. A filter unit for filtering a fluid in a sterile manner, comprising a rigid outer casing provided with at least one inlet orifice and with at least one outlet orifice, the casing enclosing a filter medium, said filter unit further comprising separate impermeable association means which connects the outer casing to the filter medium so as to define two compartments, namely an inlet compartment and an outlet compartment, wherein the association means comprises a bead of adhesive disposed between the outer periphery of the filter medium and the inside wall of the rigid outer casing.

2. A filter unit according to claim 1, wherein the association means is deformable, and in particular flexible.

3. A filter unit according to claim 1, the sheets forming the flexible frame are fixed together by a bead of sealing adhesive formed through the filter medium.

4. A filter unit according to claim 1, wherein a pre-filter or a post-filter is disposed against the filter medium, respectively on the side facing into the inlet compartment and on the side facing into the outlet compartment of the filter unit.

5. A filter unit according to claim 1, wherein the filter medium removes leukocytes from whole blood or blood components.

6. A filter unit for filtering a fluid in a sterile manner, comprising a rigid outer casing provided with at least one inlet orifice and with at least one outlet orifice, the casing enclosing a filter medium, said filter unit further comprising separate impermeable association means which connects the outer casing to the filter medium so as to define two compartments, namely an inlet compartment and an outlet compartment, wherein the association means comprises a flexible frame formed of two flexible sheets provided with openings and between which the filter medium is placed.

7. A filter unit according to claim 6, wherein the association means is sealed to the inside wall of the rigid outer casing along the outer periphery of the filter medium.

8. A filter unit according to claim 6, wherein the sheets forming the flexible frame are fixed together around the periphery of the filter medium.

9. A filter unit according to claim 6, the sheets forming the flexible frame are fixed together by a bead of sealing adhesive formed through the filter medium.

10. A filter unit according to claim 6, wherein a pre-filter or a post-filter is disposed against the filter medium, respectively on the side facing into the inlet compartment and on the ide facing into he outlet compartment of the filter unit.

11. A filter unit according to claim 6, wherein the ilter mdium remove leukocytes from whole blood or blood component.

* * * * *